United States Patent [19]

Kihara et al.

[11] Patent Number: 4,910,331
[45] Date of Patent: Mar. 20, 1990

[54] NOVEL PROCESS FOR PRODUCING THIOLSULFONIC ACID DERIVATIVES

[75] Inventors: Kazuaki Kihara; Makoto Kuroda, both of Hikari; Toshiyuki Nakamura, Kumage, all of Japan

[73] Assignee: Takeda Chemical Industries, Ltd., Osaka, Japan

[21] Appl. No.: 257,125

[22] Filed: Oct. 7, 1988

Related U.S. Application Data

[63] Continuation of Ser. No. 4,277, Jan. 6, 1987, abandoned, which is a continuation of Ser. No. 668,556, Nov. 2, 1984, abandoned.

[30] Foreign Application Priority Data

Nov. 2, 1983 [JP] Japan .................. 58-206205

[51] Int. Cl.$^4$ .......................................... C07C 143/68
[52] U.S. Cl. .................. 560/307; 548/574; 548/206; 548/146; 546/192; 546/248; 544/398; 544/161
[58] Field of Search .............. 560/307, 206; 548/574, 548/146; 546/192; 544/398, 161

[56] References Cited

U.S. PATENT DOCUMENTS

| | | | |
|---|---|---|---|
| 3,338,946 | 8/1967 | Dunbar | 260/453 RY |
| 3,346,592 | 10/1967 | Dunbar | 260/453 RY |
| 3,462,472 | 8/1969 | Dunbar et al. | 260/453 RY |

FOREIGN PATENT DOCUMENTS 45-18847  6/1970  Japan .
45-36727 11/1970  Japan .

OTHER PUBLICATIONS

Kice et al., J. Am. Chem. Soc., 89, 3557–3565 (1967).

*Primary Examiner*—Nicky Chan
*Attorney, Agent, or Firm*—Wenderoth, Lind & Ponack

[57] ABSTRACT

This invention relates to a process for producing a thiolsulfonic acid derivative of the general formula:

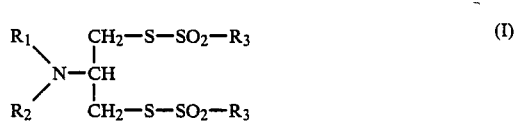

(I)

wherein each of $R_1$ and $R_2$ is independently a lower alkyl group or a 5- or 6-membered cycloalkyl group, or alternatively $R_1$ and $R_2$ together with the adjacent nitrogen atom form a 5- or 6-membered heterocyclic group which may further contain an oxygen, sulfur or nitrogen atom; and $R_3$ is (1) an aryl group which may optionally be substituted by a lower alkyl group, a halogen, a lower alkoxy group or a lower alkylthio group, (2) a lower alkyl group which may optionally be substituted by a lower alkoxy group, (3) an aralkyl group or (4) a cycloalkyl group, or a salt thereof, which comprises reacting a compound of the general formula:

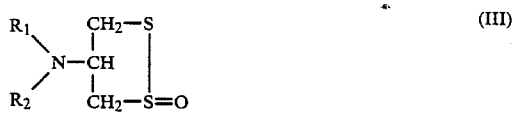

(III)

wherein $R_1$ and $R_2$ are as defined above, or a salt thereof with a compound of the general formula:

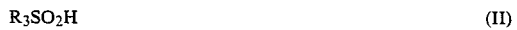

$R_3SO_2H$ (II)

wherein $R_3$ is as defined above, or a salt thereof under an acid condition.

The compound (I) or a salt thereof is produced in high purity and in high yield according to the process of this invention.

3 Claims, No Drawings

NOVEL PROCESS FOR PRODUCING THIOLSULFONIC ACID DERIVATIVES

This application is a continuation of now abandoned application Ser. No. 004,277, filed Jan. 6, 1987, which is a continuation of now abandoned application Ser. No. 668,556, filed Nov. 2, 1984.

This invention relates to a process for producing a thiolsulfonic acid derivative which possesses insecticidal, acaricidal and fungicidal activities and is of value as an agricultural chemical, particularly as a pesticide.

More particularly, this invention relates to a process for producing a thiolsulfonic acid derivative of the general formula:

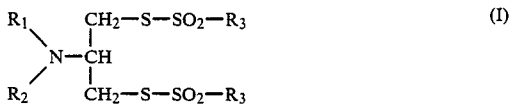

wherein each of $R_1$ and $R_2$ is independently a lower alkyl group or a 5- or 6-membered cycloalkyl group, or alternatively $R_1$ and $R_2$ together with the adjacent nitrogen atom form a 5- or 6-membered heterocyclic group which may further contain an oxygen, sulfur or nitrogen atom; and $R_3$ is (1) an aryl group which may optionally be substituted by a lower alkyl group, a halogen, a lower alkoxy group or a lower alkylthio group, (2) a lower alkyl group which may optionally be substituted by a lower alkoxy group, (3) an aralkyl group, or (4) a cycloalkyl group, or a salt thereof, which comprises reacting a compound of the general formula:

wherein $R_1$ and $R_2$ are as defined above, or a salt thereof with a compound of the general formula:

wherein $R_3$ is as defined above, or a salt thereof under an acid condition.

The objective compound (I) of this invention is known in the literature, and has been described as having strong insecticidal activities, for example in Japanese Examined Published Patent Application Nos. 18847/1970 and 36727/1970, and British Pat. No. 1264207.

The above Japanese Examined Published Pat. Application Nos. 18847/1970 and 36727/1970 describe the process which comprises reacting an N,N-dialkyl-dihalogenopropylamine with an arenethiosulfonic acid salt or alkanethiosulfonic acid salt, but the process suffers the drawbacks that the yield of the objective compound is low, while by-products are formed in large quantities, and is unsatisfactory as an industrial production.

The present inventors continued intensive research for a process which permits the compound (I) to be produced more easily in enhanced degree of purity and in increased yield, and as a result, found that the compound (III) unexpectedly reacts with the compound (II) to give the compound (I) with high degree of purity and in high yields. The finding was furthermore followed by extensive investigation, which has culminated in the present invention.

The compound (I) can be obtained in higher yield, in higher purity and with greater ease according to the process of this invention than according to the process described in Japanese Examined Published Patent Application Nos. 18847/1970 and 36727/1970.

In the above general formulae, each of $R_1$ and $R_2$ is independently a straight-chain or branched lower alkyl group of 1 to 4 carbon atoms, such as methyl, ethyl, n-propyl, isopropyl, n-butyl, isobutyl, sec-butyl or tert-butyl, or a 5- or 6-membered cycloalkyl group, such as cyclopentyl or cyllohexyl, or alternatively $R_1$ and $R_2$ together with the adjacent nitrogen atom form a 5- or 6-membered heterocyclic group which may further contain an oxygen, sulfur or nitrogen atom, such as pyrrolidine, piperidine, piperazino, morpholino or thiazolidinyl; $R_3$ is (1) an aryl group of 6 to 10 carbon atoms, such as phenyl or naphthyl, which may optionally be substituted by (a) a straight-chain or branched lower alkyl group of 1 to 4 carbon atoms, such as methyl, ethyl, n-propyl, isopropyl, n-butyl, isobutyl, sec-butyl or tert-butyl, (b) a halogen, such as fluorine, chlorine, bromine or iodine, (c) a straight-chain or branched lower alkoxy group of 1 to 4 carbon atoms, such as methoxy, ethoxy, n-propoxy, isopropoxy, n-butoxy, isobutoxy, sec-butoxy or tert-butoxy or (d) a straight-chain or branched lower alkylthio group of 1 to 4 carbon atoms, such as methylthio, ethylthio, n-propylthio isopropylthio, n-butylthio, isobutylthio, sec-butylthio or tert-butylthio, (2) a straight-chain or branched lower alkyl group of 1 to 4 carbon atoms, such as methyl, ethyl, n-propyl, isopropyl, n-butyl, isobutyl, sec-butyl or tert-butyl, which may optionally be substituted by a straight-chain or branched lower alkoxy group of 1 to 4 carbon atoms, such as methoxy, ethoxy, n-propoxy, isopropoxy, n-butoxy, isobutoxy, sec-butoxy or tert-butoxy, (3) an aralkyl group preferably of 7 to 10 carbon atoms, such as benzyl, phenethyl or phenylpropyl, or (4) a cycloalkyl group of 4 to 7 carbon atoms, such as cyclobutyl, cyclopentyl, cyclohexyl or cycloheptyl.

The aryl group $R_3$ may optionally be substituted by 1 to 3 substituents (a)–(d) described above at any position of the aryl group.

The lower alkyl group $R_3$ may optionally be substituted by 1 to 3 lower alkoxy groups at any position of the lower alkyl group.

The examples of an aryl group which is substituted by a lower alkyl group, a halogen, a lower alkoxy group, or a lower alkylthio group, represented by $R_3$ include, among others, 2-, 3- or 4-methylphenyl, 2-, 3- or 4-ethylphenyl, 2-, 3- or 4-n-propylphenyl, 2-, 3- or 4-t-butyphenyl, 2-, 3- or 4-chlorphenyl, 2-, 3- or 4-bromophenyl, 2-, 3- or 4methoxyphenyl, 2-, 3- or 4-ethoxyphenyl, 2-, 3- or 4- isopropoxyphenyl, 2-, 3- or 4-n-butoxyphenyl, 2-, 3- or 4- methylthiophenyl, 1,2-, 3- or 4-ethylthiophenyl, 2-, 3- or 4-n-propylthiophenyl, 2-, 3- or 4-isobutylthiophenyl, 2-methyl-4-chlorophenyl, 3-ethyl-4-bromophenyl, 2-chloro-4-methoxyphenyl, 2,4-dichlorophenyl, 2,4,6-trimethylphenyl and 2,4,6trichlorophenyl, 1-methyl-naphthyl, 1-chloronaphtyl, 4- methylthionaphtyl, and so on.

The examples of a lower alkyl group which is substituted by a lower alkoxy group, represented by $R_3$ include, among others, methoxymethyl, methoxyethyl, 1,-methoxypropyl, 2-methoxybutyl, ethoxylmethyl, ethoxylethyl, 2-ethoxypropyl, 3-ethoxypropyl, 1-ethoxy-1-methylpropyl, propoxymethyl, 2-isopropoxyethyl, t-butoxymethyl, 2-t-butoxyethyl, 3-t-butoxypropyl, 4-butoxybutyl and so on.

Among the above-mentioned ones, preferably, each of $R_1$ and $R_2$ is a straight-chain or branched lower alkyl group of 1 to 4 carbon atoms; and $R_3$ is an aryl group which may optionally be substituted by (a) a straight-chain or branched lower alkyl group of 1 to 4 carbon atoms, (b) a halogen, (c) a straight-chain or branched lower alkoxy group of 1 to 4 carbon atoms, or (d) a straight-chain or branched lower alkylthio group of 1 to 4 carbon atoms. More preferably, each of $R_1$ and $R_2$ is methyl; and $R_3$ is phenyl.

As the salt of the compound (I) of this invention, use is made of an agriculturally acceptable salt thereof, such as an acid addition salt with an inorganic acid, exemplified by hydrochloric acid, hydrobromic acid, sulfuric acid or phosphoric acid; or an organic acid exemplified by benzenesulfonic acid, p-toluenesulfonic acid, oxalic acid, acetic acid or maleic acid.

The compound (I) or a salt thereof is produced by reacting the compound (II) or a salt thereof with the compound (III) or a salt thereof under an acid condition, namely at pH 5 or below.

Examples of the salt of the starting compound (III) usable in the present reaction include an acid addition salt with an inorganic acid, such as hydrochloric acid, hydrobromic acid, sulfuric acid or phosphoric acid, or an organic acid, such as benzenesulfonic acid, p-toluenesulfonic acid, oxalic acid, acetic acid or maleic acid, while examples of the salt of starting compound (II) include a salt with an alkali metal, such as sodium or potassium, an alkaline earth metal, such as calcium or magnesium, and ammonium radical.

The starting compound (III) or a salt thereof may exist in four kinds of stereoisomers due to the presence of an asymmetric carbon atom and a $>S=O$ (sulfoxide) bond in the molecule. These four then kinds of stereoisomers may be used after separating into individual optically active isomers or as a mixture of such optically active isomers.

In this reaction, the starting compound (II) or a salt thereof can be employed in an amount of from about 2 moles to a large excess per mole of starting compound (III) or a salt thereof.

In order to maintain this reaction in the acid pH range of not more than 5, use is made of e.g. an inorganic acid, such as hydrochloric acid, hydrobromic acid, sulfuric acid or phosphoric acid, or an organic acid, such as benzenesulfonic acid, p-toluenesulfonic acid, oxalic acid or maleic acid. The acid is added in such an amount as to maintain the pH value of the reaction mixture at not more than 5. For example, it is desirable, in the case of the reaction in water or a mixed solvent of water and an organic solvent described below, to add the acid in such a manner as the acid concentration of the reaction mixture may be in the range of about 0.1 to 3 normal. The acid may be added at once when the reaction is initiated, or may be added little by little in such a wa as to maintain the pH value of the reaction mixture in the acid range, as the reaction proceeds.

The reaction is normally carried out in a solvent. The suitable solvent may be any type of solvent, unless it adversely affects the reaction. Use is made of, for example, water or an organic solvent, such as acetic acid, a lower alcohol of 1 to 3 carbon atoms, such as methyl alcohol, ethyl alcohol or isopropyl alcohol, acetone, acetonitrile, dimethylformamide or dimethylsulfoxide, solely or as a mixture of two or more solvents. Of these, water, acetic acid and a mixed solvent of water and acetic acid are preferable.

The reaction proceeds usually at about 5° C. to room temperature (about 15° C.), or the reaction may be carried out at about 60° to 100° C. The reaction time varies with the reaction temperature, etc., and is normally in the range of 30 minutes to 4 hours.

The reaction may be conducted in the absence of a sulfide catalyst.

The compound (I) or a salt thereof thus obtained is isolated and purified by means known per se, such as distillation, distillation under reduced pressure, solvent extraction, pH adjustment, solvent-transformation, concentration, concentration under reduced pressure, crystallization, recrystallization and/or chromatography. More concretely, after the conclusion of the reaction, the reaction mixture is adjusted, under cooling or heating, to the pH in the neighborhood of 4 to 6, if necessary with an aqueous solution of a suitable alkali (e.g. sodium hydroxide, potassium hydroxide, etc.), and by such procedure, the compound (I) can be isolated as crystals with a high degree of purity. Or, as the case may be, the reaction mixture is concentrated by distilling off the organic solvent, and the residue is neutralized with an aqueous solution of a suitable alkali (e.g., sodium hydroxide, potassium hydroxide, etc.) in the presence of an organic solvent immiscible with water, such as ether, chloroform or benzene; then, the mixture is separated into two phases and the organic layer is separated out; and subsequently, by following a conventional procedure known per se, the compound (I) may be crystallized.

In cases in which the compound (I) is difficult to be crystallized, the compound (I) can be isolated as a crystalline salt by adding an inorganic acid, such as hydrochloric acid, or an organic acid, such as oxali acid, p-toluenesulfonic acid or picric acid to the organic layer separated from two phases as mentioned above.

The starting compound (III) or a salt thereof can be produced by a method known per se, such as the method as described in Agr. Biol. Chem., 34, 935-940 (1974).

Thus, the compound (III) or a salt thereof is produced by oxidizing a compound of the general formula:

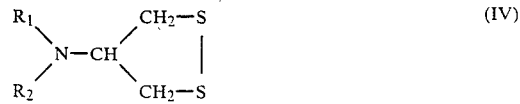

wherein each of the symbols is as defined above, or a salt thereof, with an oxidizing agent under an acid condition. Examples of the salt of the compound (IV) include a salt with an inorganic acid, such as hydrochloric acid, sulfuric acid or hydrobromic acid, or an organic acid, such as maleic acid, oxalic acid, fumaric acid or p-toluenesulfonic acid, etc.

As the oxidizing agent in this reaction, use is made of organic and inorganic peracids. More concretely, use is made of an organic peracid, such as a percarboxylic acid, e.g. performic acid, peracetic acid, trifluoroperacetic acid, permaleic acid, perbenzoic acid, m-chloroperbenzoic acid or monoperphthalic acid; or a persulfonic acid, e.g. p-toluenepersulfonic acid, and an inorganic peracid, such as hydrogen peroxide, periodic acid or persulfuric acid. These organic and inorganic peracids are employed solely or as a mixture of two or more kinds of peracids. Among these, hydrogen peroxide is preferable. The oxidizing agent is normally used in an amount of at least an equivalent amount, preferably about 1.1 to 1.2 moles per mole of the compound (IV). However, it is likewise possible to employ the oxidizing agent in an amount of from 3 moles to a large excess per mole of the compound (IV). This oxidation reaction is normally carried out in an inert solvent. Selection of the solvent varies depending particularly upon the solubility of the starting materials and type of the oxidizing agent, and for example, dichloromethane, chloroform, dimethylformamide, eetrahydrofuran, acetonitrile, water, acetic acid, ethyl acetate, etc. are used solely or as a mixed solvent consisting of these. Among the above solvents, particularly, water and acetic acid are preferable.

The reaction temperature ranges from about −10° to 60° C., preferably from about 0° to 40° C. The reaction time is in the range of about 1 to 4 hours.

After the conclusion of the reaction using, for example, water or a mixture of water and organic solvent as the reaction solvent, the reaction mixture can be used in the subsequent reaction, as such and also after adding an organic solvent immiscible with water, such as benzene, chloroform or ether, neutralizing the resultant mixture with an aqueous solution of a suitable alkali (e.g., sodium hydroxide, potassium hydroxide, etc.) under cooling and concentrating the organic layer resulting after separation into the aqueous and organic phases to isolate the compound (III) as a free base form. Furthermore, the compound isolated b the above procedure may be made into a salt with an inorganic acid, such as hydrochloric acid, sulfuric acid or hydrobromic acid, or an organic acid, such as maleic acid, oxalic acid, fumaric acid or p-toluenesulfonic acid, according to a per se convention method, and then may be used in the subsequent reaction.

The starting compound (II) or a salt thereof has already been known in the literature, and is produced, for example, by the method as described in Organic Synthesis collective Vol. IV, page 674 or Japanese Unexamined Published Patent Application No. 7753/1981. For example, the compound (II) is produced according to the method shown below.

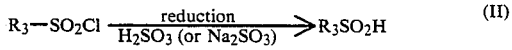

$$R_3\text{—}SO_2Cl \xrightarrow[\text{H}_2\text{SO}_3 \text{ (or Na}_2\text{SO}_3\text{)}]{\text{reduction}} R_3SO_2H \qquad (II)$$

wherein $R_3$ is as defined above.

The starting compound (IV) is produced by per se known methods, e.g. a method described in Agr. Biol. Chem., 34, 935 (1970).

The thus obtained starting compounds are isolated and purified by means known per se, such as distillation, distillation under reduced pressure, solvent extraction, pH adjustment, solvent-transformation, crystallization, recrystallization and/or chromatography.

This invention is illustrated by the following nonlimiting examples.

The term "%" means weight % unless otherwise specified.

In the examples, etc., the NMR spectra are measured at 60 MHz (solvent: d-trifluoroacetic acid) and expressed as $\tau$ value, whereby the symbols used herein have the following respective meanings: s, singlet; d, doublet; t, triplet; qr, quartet; ABqr, AB pattern quartet; qn, quintet; m, multiplet; J, coupling constant.

REFERENCE EXAMPLE 1

Production of 4-(N,N-dimethylamino)-1,2-dithiolane-1-oxide hydrochloride.

47.8 g of 4-(N,N-dimethylamino)-1,2-dithiolane oxalate is dissolved in 200 ml of water. 75 ml of benzene is added to the solution, and the mixture is neutralized with 35 ml of a 28% aqueous sodium hydroxide solution under stirring, while maintaining the temperature of the mixture in the neighborhood of 25° C. The neutralized solution is filtered to separate into crystals and filtrate. The crystals are furthermore washed well with 25 ml of benzene, and the washing is combined with the filtrate as separated previously, followed by separation into the benzene and aqueous layers. The benzene layer is extracted with 58 ml of 15% hydrochloric acid, and the aqueous extract is combined with the aqueous solution as separated previously. While maintaining the temperature of the aqueous solution at 10° C., 22 g of a 30% aqueous hydrogen peroxide solution is added dropwise to the solution with stirring over the period of about 1 hour. After the addition is completed, stirring is carried out at room temperature for 1 hour. High performance liquid chromatographic analysis of this solution shows that the content of the title compound is 39.6 g (yield 98%). The reaction solution is almost concentrated to dryness under reduced pressure, and after 150 ml of ethanol is added to the residue to bring into a slurry form, the powder obtained by filtration is dried to give 34.3 g (yield of 85%) of the title compound.

I.R. $\nu_{max}^{KBr}$ cm$^{-1}$: 1078
UV $\lambda_{max}^{H_2O}$ nm: 241
NMR: 5.7–6.5(5H, m), 6.92(6H, s)
m.p.: 152.5°–167° C. (decomp.)

By the same procedure as described above, the following compounds are produced.

4-(N,N-Diethylamino)-1,2-dithiolane-1-oxide hydrochloride;
I.R. $\nu_{max}^{KBr}$ cm$^{-1}$:1080
NMR: 5.52(1H, qn), 6.48(4H, d, J=5.5 Hz), 6.56(4H, qr), 8.47(6H, t, J=7.0 Hz). 4-(N,N-Methylethylamino)-1,2-dithiolane-1-oxide hydrochloride;
I.R. $\nu_{max}^{KBr}$ cm$^{-1}$: 1085
NMR: 5.56(1H, qn), 6.44(4H, d, J=6.0 Hz), 6.65(2H, qr), 7.05(3H, s), 8.62(3H, t, J=7.0 Hz).
4-(N,N-Methylcyclohexylamino)-1,2-dithiolane-1-oxide hydrochloride;
I.R. $\nu_{max}^{KBr}$ cm$^{-1}$: 1087
NMR: 5.52(1H, m), 6.38(4H, d, J=7.0 Hz), 6.59(1H, m), 7.5–6.96(3H, d, J=5 Hz), 7.5–8.5(10H, m)
4-(N,N-Dicyclohexylamino)-1,2-dithiolane-1-oxide hydrochloride;
I.R. $\nu_{max}^{KBr}$ cm$^{-1}$: 1093
NMR: 5.55(1H, m), 6.40(4H, d, J=6.5 Hz), 6.90(2H, m), 8.0–9.2(20H, m).
4-(N,N-Piperidino)-1,2-dithiolane-1-oxide hydrochloride; I.R. $\nu_{max}^{KBr}$ cm$^{-1}$: 1095
NMR: 5.58(1H, m), 6.46(4H, d, J=5.5 Hz), 5.9–7.1(4H, m), 7.98(6H, m).
4-Morpholino-1,2-dithiolane-1-oxide hydrochloride;
I.R. $\nu_{max}^{KBr}$ cm$^{-1}$: 1098
NMR: 5.58(1H, m), 5.70(4H, m), 6.24(4H, m), 6.43(4H, d, J=5.0 Hz).

EXAMPLE 1

Production of S,S'-[2-(dimethylamino)trimethylene]bis-benzenethiosulfonate

In 150 ml of water is dissolved 68.9 g of sodium benzenesulfinate, while stirring. To the solution is added 76.7 ml of 20% hydrochloric acid to make a benzenesulfinic acid solution, to which 134.4 ml of a 30 w/v % aqueous solution of 4-(N,N-dimethylamino)-1,2-dithiolane-1-oxide hydrochloride is added. To the mixture is added 97 ml of 20% hydrochloric acid, followed by stirring at 50° C. for 4 hours. After the completion of the reaction, the reaction mixture, while maintaining the temperature in the neighborhood of 50° C., is gradually neutralized with a 28% aqueous sodium hydroxide solution, whereby the pH is kept at 4. The end-point of neutralization is at the point of time when the aqueous sodium hydroxide solution is hardly consumed, and the amount of a 28% aqueous sodium hydroxide solution consumed is about 140 ml, with 2 to 3 hours being required for the neutralization. After the conclusion of the neutralization, crystals which separate out are filtered, washed with 200 ml of water and dried to give the title compound. Crop 84.6 g (yield of 98.0%). m.p.: 82°–83° C.

EXAMPLE 2

Production of S,S'-[2-(dimethylamino)trimethylene]bis-benzenethiosulfonate.

To 100 ml each of the below-described solvents are added 34.5 g of sodium benzenesulfinate and 38.4 ml of 20% hydrochloric acid to make a benzenesulfinic acid solution. 16.5 g of crystalline 4-(N,N-dimethylamino)-1,2-dithiolane-1-oxide hydrochloride is added to the solution, and 50 ml of 20% hydrochloric acid is further added, followed by reaction at 60° C. for 1.5 hours. After the conclusion of the reaction, the solvent is distilled off under reduced pressure, and 150 ml of water is added to the residue to bring into a slurry, to which a 28% aqueous sodium hydroxide solution is added for neutralization.

Thereafter, the same procedure as in Example 1 is conducted to give the title compound.

The solvents employed, together with the yields, are shown in the following.

| Type of solvent | Acetic acid | Ethanol | Acetonitrile | Dioxane | DMF |
|---|---|---|---|---|---|
| Crop, g | 42.8 | 41.9 | 42.2 | 41.8 | 41.9 |
| Yield, % | 99.2 | 97.1 | 97.7 | 96.8 | 97.0 |

EXAMPLE 3

Shown below are the thiolsulfonic acid derivatives obtained by the same procedure as described in Example 1.

(1) S,S'-[2-(Dimethylamino)trimethylene]bis-ethylthiosulfonate. yield 95%, m.p. 78.5°–80° C. (decomp.).
Elemental analysis, for $C_{11}H_{27}NO_4S_4$: Calcd.: C, 28.62; H, 5.89; N, 3.03 (%).
Found: C, 28.62; H, 5.90; N, 3.03 (%).
IR $\nu_{max}^{KBr}$ cm$^{-1}$: 1315, 1130
NMR: 5.85(1H, m), 6.24(4H, d, J=6.0 Hz), 6.79(6H, d, =5.0 Hz), 6.39(4H, qr.), 8.43(6H, t, J=7.0 Hz).

(2) S,S'-[2-(Dimethylamino)trimethylene]bis-β-ethoxyethylthiosulfonate.
Elemental analysis, for $C_{13}H_{29}NO_6S_4$: Calcd.: C, 36.86; H, 6.90; N, 3.30 (%). Found: C, 36.42; H, 7.05; N, 3.70 (%).
IR $\nu_{max}^{liquid\,film}$ cm$^{-1}$: 1320, 1120
NMR: 6.68(5H, s), 7.65(6H, s).

(3) S,S'-[2-(Dimethylamino)trimethylene]bis-benzylthio-sulfonate oxalate yield. 90%, m.p. 151° C. (decomp.).
Elemental analysis, for $C_{21}H_{27}NO_8S_4$: Calcd.: C, 45.88; H, 4.95; N, 2.55 (%). Found: C, 45.58; H, 4.90; N, 2.51 (%).
IR $\nu_{max}^{KBr}$ cm$^{-1}$: 1320, 1130
NMR: 2.43(10H, s), 5.23(4H, m) 6.60(1H, m), 7.15(4H, d, J=6.0 Hz), 7.19(6H, d, J=5.0 Hz).

(4) S,S'-[2-(Dimethylamino)trimethylene]bis-p-toluenethiosulfonate. yield 92%, m.p. 114°–115° C.
Elemental analysis, for $C_{19}H_{25}NO_4S_4$: Calcd.: C, 49.64; H, 5.48; N, 3.05 (%). Found: C, 49.74; H, 5.69; N, 3.03 (%).
IR $\nu_{max}^{KBr}$ cm$^{-1}$: 1320, 1134
NMR: 2.21, 2.66(8H, ABqr, J=8 Hz), 6.99(5H, s), 7.55(6H, s), 7.83(6H, s).

(5) S,S'-[2-(Dimethylamino)trimethylene]bis-p-chlorobenzenethiosulfonate. yield, 95%, m.p. 143°–144° C.
Elemental analysis, for $C_{17}H_{19}Cl_2NO_4S_4$: Calcd.: C, 40.79; H, 3.83; N, 2.80 (%). Found: C, 41.04; H, 3.79; N, 2.53 (%).
IR $\nu_{max}^{KBr}$ cm$^{-1}$: 1324, 1143
NMR: 2.13, 2.42(8H, ABqr, J=9.0 Hz), 6.92(5H, s), 7.78(6H, s).

(6) S,S'-[2-(Dimethylamino)trimethylene]bis-p-methoxybenzenethiosulfonate. yield 90%, m.p. 115.5°–117° C.
Elemental analysis, for $C_{19}H_{25}NO_6S_4$: Calcd.: C, 48.53; H, 5.62; N, 2.69 (%). Found: C, 48.33; H, 5.59; N, 2.58 (%).
IR $\nu_{max}^{KBr}$ cm$^{-1}$: 1326, 1137
NMR: 2.14, 2.94(8H, ABqr, J=9.0 Hz), 6.08(6H, s), 6.79(5H, s), 7.80(6H, s).

(7) S,S'-[2-(Dimethylamino)trimethylene]bis-p-methylbenzenethiosulfonate. yield 91%, m.p. 102°–104° C.
Elemental analysis, for $C_{19}H_{25}NO_4S_6$: Calcd.: C, 43.57; H, 4.81; N, 2.67 (%). Found: C, 43.34; H, 4.76; N, 2.54 (%).
IR $\nu_{max}^{KBr}$ cm$^{-1}$: 1320, 1142
NMR: 2.22, 2.68(8H, ABqr, J=8.5 Hz), 6.97(5H, s), 7.46(6H, s), 7.82(6H, s).

(8) S,S-[2-(Dimethylamino)trimethylene]bis-β-naphthylthiosulfonate. yield 90%, m.p. 110°–115° C.
Elemental analysis, for $C_{25}H_{25}NO_4S_4$: Calcd.: C, 56.47; H, 4.74; N, 2.63 (%). Found: C, 56.07; H, 4.68; N, 2.60 (%).
IR $\nu_{max}^{KBr}$ cm$^{-1}$: 1313, 1122
NMR: 1.85–2.4(14H, m), 6.93(5H, s), 7.87(6H, s).

(9) S,S'-[2-(Methylethylamino)trimethylene]bis-p-toluenethiosulfonate. yield 89%, m.p. 97°–98° C.
Elemental analysis, for $C_{20}H_{27}NO_4S_4$: Calcd.: C, 50.71; H, 5.74; N, 2.96 (%). Found: C, 50.45; H, 5.58; N, 2.79 (%).
IR $\nu_{max}^{KBr}$ cm$^{-1}$: 1320, 1135
NMR: 2.16, 2.61(4H, ABqr, J=8.5 Hz), 6.92(5H, s), 7.58(2H, qr), 7.62(6H, s), 7.86(3H, s), 9.09(3H, t, J=7.0 Hz).

(10) S,S'-[2-(Methylcyclohexylamino)trimethylene]bis-p-toluenethiosulfonate. yield 91%, m.p. 120°–121° C.

Elemental analysis, for $C_{26}H_{35}NO_4S_4$: Calcd.: C, 50.55; H, 5.71; N, 2.27 (%). Found: C, 50.32; H, 5.73; N, 2.31 (%).

IR $\nu_{max}^{KBr}$ cm$^{-1}$: 1330, 1140.

NMR: 2.07, 2.47(4H, ABqr, J=8.5 Hz), 5.49(1H, m), 6.38(4H, d, J=7.0 Hz), 6.59(1H, m), 6.96(3H, d, J=5.0 Hz), 7.36(6H, s), 7.5–8.7(10H, m).

(11) S,S'-[2-(Dicyclohexylamino)trimethylene]bis-p-toluenethiosulfonate. yield 92%, m.p. 104°–106° C.

Elemental analysis, for $C_{29}H_{41}NO_4S_4$: Calcd.: C, 58.45; H, 6.93; N, 2.35 (%). Found: C, 58.39; H, 6.91; N, 2.33 (%).

IR $\nu_{max}^{KBr}$ cm$^{-1}$: 1325, 1140

NMR: 2.14, 2.60(4H, ABqr, J=8.5 Hz), 6.90(5H, s), 6.90(2H, m), 7.52(6H, s), 8.0–9.2(20H, m).

(12) S,S'-[2-Piperidino-trimethylene]-bis-p-toluenethiosulfonate. yield 95%, m.p. 122°–123° C.

Elemental analysis, for $C_{22}H_{29}NO_4S_4$: Calcd.: C, 52.87; H, 5.85; N, 2.80 (%). Found: C, 52.76; H, 5.72; N, 2.82 (%).

IR $\nu_{max}^{KBr}$ cm$^{-1}$: 1315, 1140

NMR: 2.22, 2.65(4H, ABqr, J=8.5 Hz), 6.96(5H, s), 7.68(4H, m), 8.60(6H, m).

(13) S,S'-[2-Morphoiino-trimethylene]-bis-p-toluenethiosulfonate. yield 95%, m.p. 124°–125° C.

Elemental analysis, for $C_{23}H_{31}NO_4S_4$. Calcd.: C, 53.77; H, 6.08; N, 2.73 (%). Found: C, 53.55; H, 6.33; N, 2.67 (%).

IR $\nu_{max}^{KBr}$ cm$^{-1}$: 1320, 1135

NMR: 2.21, 2.63(4H, ABqr, J=8.0 Hz), 6.42(4H, m), 6.93(5H, s), 6.93(4H, m), 7.54(6H, s).

What is claimed is:

1. A process for producing a thiolsulfonic acid derivative of the formula:

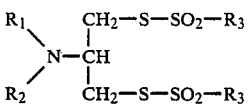

wherein each of $R_1$ and $R_2$ is independently alkyl of 1 to 4 carbon atoms or a 5- or 6-membered cycloalkyl group, or $R_1$ and $R_2$ together with the adjacent nitrogen atom form pyrrolidino, piperidino, piperazino, morpholino or thiazolidinyl; and $R_3$ is (1) aryl of 6 to 10 carbon atoms which is unsubstituted or substituted by alkyl of 1 to 4 carbon atoms, halogen, alkoxy of 1 to 4 carbon atoms or alkylthio of 1 to 4 carbon atoms, (2) alkyl of 1 to 4 carbon atoms which is unsubstituted or substituted by alkoxy of 1 to 4 carbon atoms, (3) aralkyl or (4) cycloalkyl of 4 to 7 carbon atoms, or a salt thereof, which consists essentially of reacting a compound of the formula:

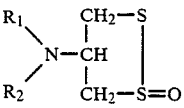

wherein $R_1$ and $R_2$ are as defined above, or a salt thereof, with a compound of the formula:

wherein $R_3$ is as defined above, or a salt thereof, under an acid condition in the absence of a sulfide catalyst.

2. A process as claimed in claim 1, wherein each of $R_1$ and $R_2$ is independently methyl, add $R_3$ is phenyl.

3. A process as claimed in claim 1, wherein the acid condition is pH 5 or below.

* * * * *